United States Patent [19]

Jagoutz et al.

[11] 4,121,098

[45] Oct. 17, 1978

[54] RADIATION ANALYSIS APPARATUS AND METHOD UTILIZING MULTI-CHANNEL PULSE PEAK VOLTAGE DISCRIMINATOR

[75] Inventors: Emil Jagoutz, Mainz-Gonsenheim; Christl Palme, Mainz, both of Germany

[73] Assignee: Max-Planck-Gesellschaft zur Förderung der Wissenschaften e.V., Gottingen, Germany

[21] Appl. No.: 782,564

[22] Filed: Mar. 29, 1977

[30] Foreign Application Priority Data

Jan. 28, 1977 [DE] Fed. Rep. of Germany ....... 2703562

[51] Int. Cl.² .......................... G01N 23/20; G21K 1/00
[52] U.S. Cl. ...................................... 250/273; 250/272
[58] Field of Search ............... 250/272, 273, 277, 278, 250/279

[56] References Cited

U.S. PATENT DOCUMENTS

| 2,802,947 | 8/1957 | Hamacher | 250/273 X |
|---|---|---|---|
| 3,107,297 | 10/1963 | Wittry | 250/279 |
| 3,365,574 | 1/1968 | Duncumb | 250/272 X |
| 3,790,792 | 2/1974 | Ishijima | 250/278 |
| 3,806,726 | 4/1974 | Ishijima | 250/273 X |

Primary Examiner—Alfred E. Smith
Assistant Examiner—Janice A. Howell
Attorney, Agent, or Firm—Flynn & Frishauf

[57] ABSTRACT

A radiation detector such as a proportional counter produces pulses of which the peak voltage is representative of radiation energy and the pulse rate is representative of radiation intensity. These pulses are sorted out according to peak voltage and the pulses in each peak voltage range are individually counted. Each channel has an AND-gate with one input receiving a signal from a flipflop which is set when a differential amplifier of that channel detects an input pulse voltage exceeding a predetermined bias and the AND-gate also has another input connected to the negative output of the flipflop of the next higher channel. The bias voltage of differential amplifiers sets the lower threshold of each channel, of which the upper threshold is the lower threshold of the next higher channel. When a transfer pulse is applied to the AND-gates, only the counter of the channel for the range within which the peak voltage of the detected pulse lies receives a pulse. All of the flipflops are reset at the end of the transfer pulse.

10 Claims, 4 Drawing Figures

RADIATION ANALYSIS APPARATUS AND METHOD UTILIZING MULTI-CHANNEL PULSE PEAK VOLTAGE DISCRIMINATOR

This invention concerns a method and an apparatus for radiation analysis dealing with radiation which can readily be converted by a suitable detector into a sequence of pulses in which the peak pulse voltage is representative of the energy of radiation and the rate of pulse occurrence is representative of the intensity of the radiation. Such radiation is found, for example, in X-ray fluorescence of various materials under various kinds of energetic radiation.

In the known analysis equipment for X-ray fluorescence the energy distribution of the fluorescence radiation with reference to the wave length is determined by means of a refracting crystal. The component of a beam of X-ray fluorescence which is refracted at a particular angle that can be varied in the apparatus (which is to say the component of the beam that has a wave length corresponding to the refraction angle) is converted into an electric pulse signal by an X-ray detector such as a counter tube (the well-known proportional counter). The processing of the pulses is carried out with the use of a sin $\theta$-potentiometer at the output of which is connected a single channel pulse voltage discriminator. The pulses are attenuated by the factor $1/\sin\theta$ by the action of the potentiometer, so that the pulse height of the characteristic radiation is independent from the Bragg refraction angle and therefore the voltage range to which the single-channel discriminator responds does not have to be continually readjusted in accordance with the measuring angles. The sin$\theta$-potentiometer can also be omitted, in which case the response range of the single-channel discriminator is either manually or mechanically adjusted or the compensation is provided in the processing of the pulse signal by the interposition of a program-controlled computer, as disclosed in volume 41, J. Sci. Inst. p. 15 (1964).

The known X-ray fluorescence analysis equipments have the disadvantage that with them it is not possible to separate a background radiation from the characteristic X-ray fluorescence radiation that is of interest. In many cases, even by careful adjustment of the single-channel pulse height discriminator no separation can be obtained of the signal pulse peaks of interest from the crystal fluorescence radiation, higher orders of refraction, and their escape peaks. Furthermore, for each fixed setting of the single-channel pulse height discriminator no drift of the thresholds may be allowed to take place in the apparatus during measurement.

It is an object of the present invention to overcome the disadvantages above described and to provide a method and appartus for X-ray fluorescence analysis and the like which makes possible trouble-free separation of the useful signals from disturbing signals by means of relatively simple devices and arrangements.

SUMMARY OF THE INVENTION

Briefly, the output of the radiation detector illuminated by the refracted radiation beam is supplied to a multi-channel peak voltage discriminator in which the pulses produced by the detector are sorted out according to a scale of peak voltage ranges, one output channel for each range. Each channel output of the multi-channel discriminator is supplied to an individual counter. It is particularly advantageous to provide the peak voltage discriminator in a form comprising for each channel a differential amplifier, a bistable circuit (flipflop), and a coincidence circuit, succeeding each other in that order. The radiation detector output is supplied to one input of each of the differential amplifiers, the respective other inputs being connected to a set of bias voltage sources setting the lower threshold for the respective peak voltage ranges to be detected. The outputs of the respective differential amplifiers are supplied to the set (S) inputs of the respective following bistable circuits, the outputs of one particular polarity of which are respectively supplied to the following coincidence circuits. The upper threshold of the peak voltage range of each channel is provided by connecting the output of the other polarity of the bistable circuit of the next higher channel, if there is one, to another input of the coincidence circuit. A transfer gating signal is provided to still another input of the coincidence circuit by a timing circuit triggered by the same pulses which are supplied to the differential amplifiers by the radiation detector and as soon as the short transfer gate has had time to be effective, another output of the timing circuit resets all of the bistable circuits so that they will be ready for the response to the next pulse.

The system and method of the invention has the advantage that the outputs of all the counters that respond to the respective output channels of the discriminator can be simultaneously displayed visually, on a picture tube for instance, or can be recorded automatically in parallel traces of a recorder. From the side-by-side display of the number of pulses in the respective peak voltage ranges it is easy to see how much is the contribution of the background radiation and the like and how much is the contribution of the particular rays of interest. Furthermore, the relatively considerable mechanical complication and expense involved in the use of a sin$\theta$-potentiometer is avoided and a high level of reliability is obtained in the practice of the invention because of the purely electronic character of the pulse processing method and apparatus.

The invention is further described by way of example with reference to the accompanying drawings, in which.

Figure 1:
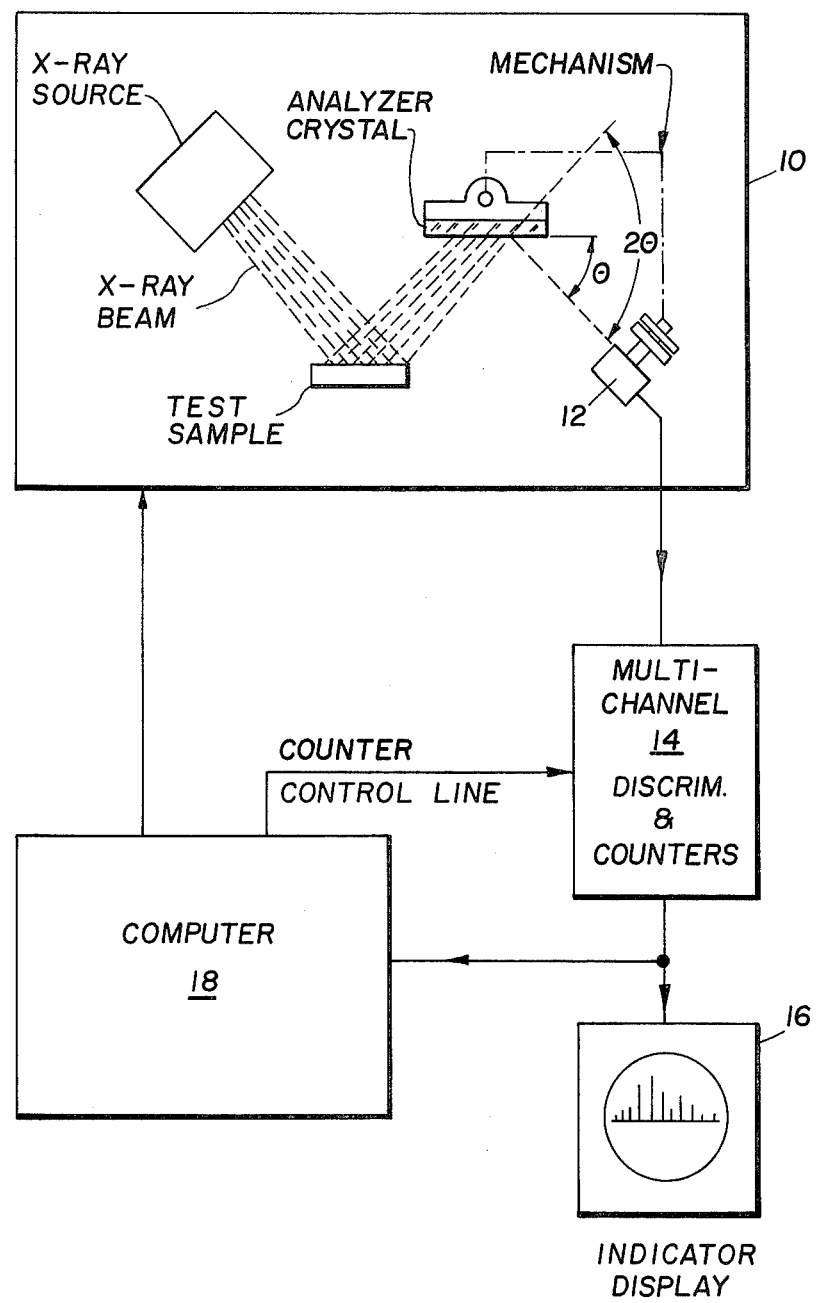
FIG. 1 is a basic diagram of an apparatus for X-ray fluorescence analysis in accordance with the invention.

The portion of the apparatus of FIG. 1 within the rectangle 10 is a conventional set-up for producing a sequence of pulses in response to a particular wave length component of a beam or bundle of X-rays produced by fluorescence of an irradiated sample material, the wave length being selected by the particular angle at which radiation is refracted by an analyzer crystal, which is to say the particular angle of tilt at which the analyzer crystal is set to refract the radiation into the narrow input of the detector 12.

Figure 2:
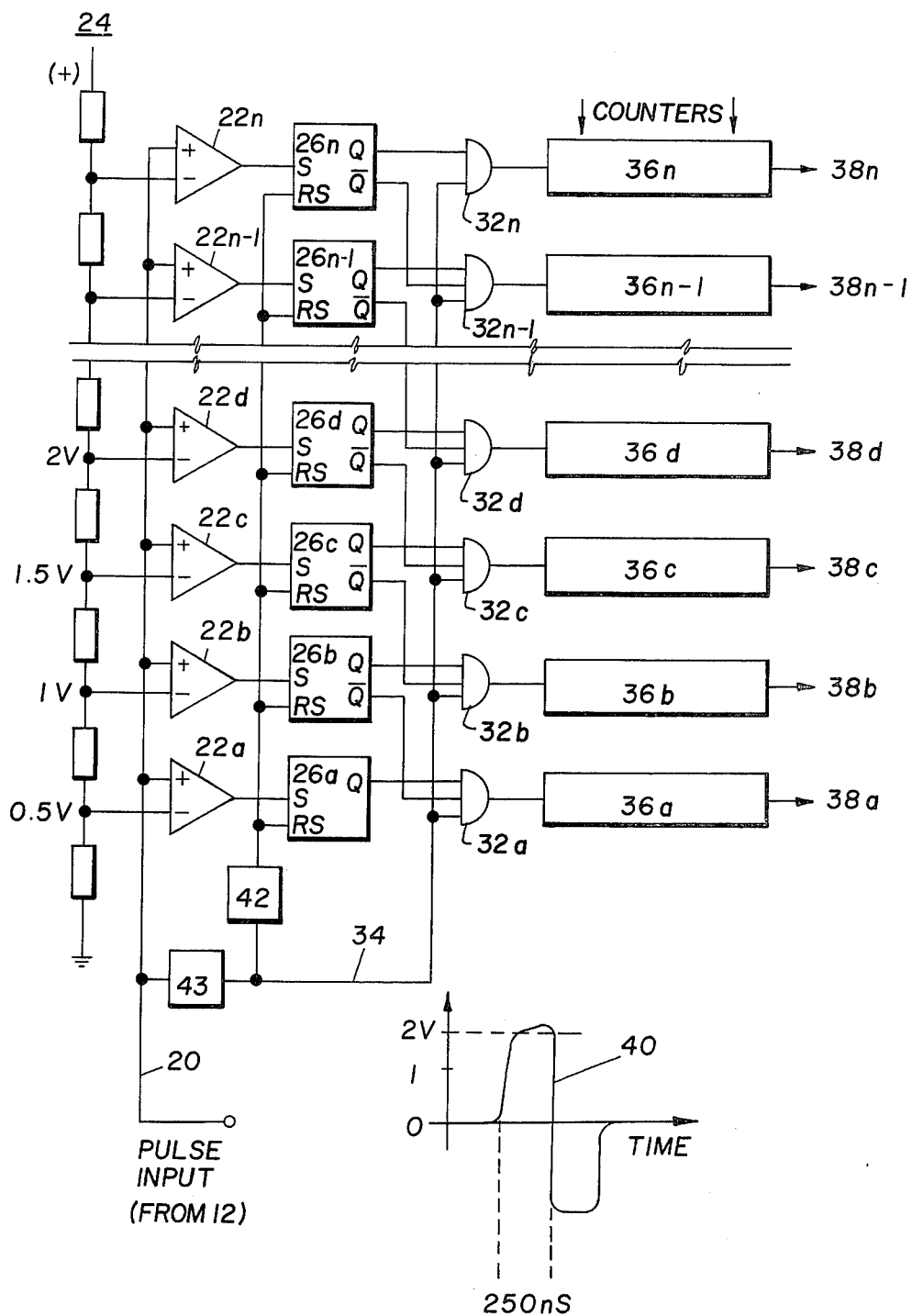
FIG. 2 is a circuit diagram of a multi-channel pulse height discriminator in accordance with the invention that is particularly suited for the apparatus of FIG. 1.

Unlike the conventional apparatus, however, the output of the diagrammatically represented X-ray detector 12 is not connected to a sin$\theta$-potentiometer and/or a single-channel pulse height discriminator, but rather with a multi-channel pulse height discriminator 14 that hereinafter will be simply referred to as a multi-channel discriminator and is preferably constituted as shown in FIG. 2.

The multi-channel measurement results produced by the multi-channel discriminator 14 can be displayed visually, as indicated by the provision of the display device 16 in FIG. 1 and/or it can be processed by a program-controlled computer 18 that can also serve for control of the conduct of the measuring process, for example, the substitution of succeeding samples for observation in the equipment 10, the angular setting of the refracting crystal, the measuring periods of the multi-channel discriminator and even the peak voltage range settings defining the channels.

As shown in FIG. 2, the pulses produced at the output of the X-ray detector 12 are supplied over a connection 20 to the respective non-inverting inputs of a multiplicity of differential amplifiers 22a to 22n that correspond in number to the output channels of the discriminator. In practice it is sufficient and convenient to utilize somewhere between about 20 and about 100 channels in such a discriminator. The inverting inputs of the respective differential amplifiers 22a to 22n are, as shown, connected to different taps of a resistance voltage divider 44, so that reference voltages increasing by steps are applied to respective channels corresponding to progressively higher input thresholds.

The outputs of the differential amplifiers 22a to 22n are respectively connected with the set inputs S of a corresponding group of bistable flipflop circuits 26a to 26n. The respective Q outputs of each of these bistable circuits which produce an output signal when the bistable circuit is in the set condition, are connected to the respective members of a corresponding group of coincidence circuits 32a to 32n that may also be referred to as AND-gates. The coincidence circuits 32a to 32n −1 also have a second input connected to the $\overline{Q}$ output of the bistable circuit of the next higher channel. That output provides an output signal in each case when the bistable circuit is in its not-set condition (sometimes referred to as the reset condition). The next higher channel is defined as the channel which the differential amplifier has its input threshold on the next higher tap of the voltage divider 24. Thus the AND-gate 32a, for example, has one of its inputs connected to the $\overline{Q}$ output of the flipflop circuit 26b. Finally, another input of each of the coincidence circuits 32a to 32n is connected to a transfer pulse bus 34 that controls the transfer of the signals produced by the respective bistable circuits 26 to the corresponding counters 36 of the various channels. The transfer pulses are produced by a pulse-shaping and delay circuit 43 in response to the input pulses received over the connection 20 from the X-ray detector 12. The transfer pulse bus 34 is also connected through a delay circuit 42 with the reset input RS of each of the bistable circuits 26a to 26n, so that the respective Q outputs of all of the bistable circuits are set back to zero after the transfer of the pulse stored in one of the bistable circuits to the corresponding counter has taken place.

The multi-channel discriminator shown in FIG. 2 operates as follows. When an input pulse represented by the typical wave form 40 at the bottom of the diagram appears on the input connection 20, the potential at the non-inverting inputs of all of the differential amplifiers 22a to 22n rises with the pulse voltage. All of those differential amplifiers at which the potential goes beyond the bias provided at the inverted input of the same differential amplifier deliver an output signal. In the case of the pulse 40 represented in the figure, which has an amplitude of somewhat more than +2V, the differential amplifiers 22a to 22d will therefore deliver an output pulse. These output pulses then set the corresponding bistable circuits 26a to 26d. Immediately thereafter the transfer pulse appears on the transfer bus 34. This pulse can turn on only one of the coincidence circuits (in the assumed example, the AND-gate 32d) which corresponds to the relatively highest tap (in the example, 2V) of the voltage divider among the responding channels, because the "lower" AND-gates are blocked by the signal produced at the inverting output $\overline{Q}$ of the bistable circuit of the next higher channel. Of course at the same time the coincidence circuits of the still "higher" channels (in the assumed example, the coincidence circuits 32e to 32n) are likewise blocked because there is a no signal at the Q output of the corresponding bistable circuit.

Upon the appearance of a transfer pulse on the bus 34, a signal will be transferred into only one counter (in the example, 36d). Thus it may be said that the input pulse has been sorted out into the proper channel and stored in the counter that corresponds to the pulse amplitude (peak voltage). After the transfer of the pulse into the corresponding counter, all of the bistable circuits 26 that were previously set are reset by the delayed pulse produced by the delay circuit 42 and the discriminator circuit is ready for processing (sorting) the next pulse.

The starting and reseting of the counter 36 can be controlled by the computer 18 by a counter control connection diagrammatically shown in FIG. 1.

Figure 3:
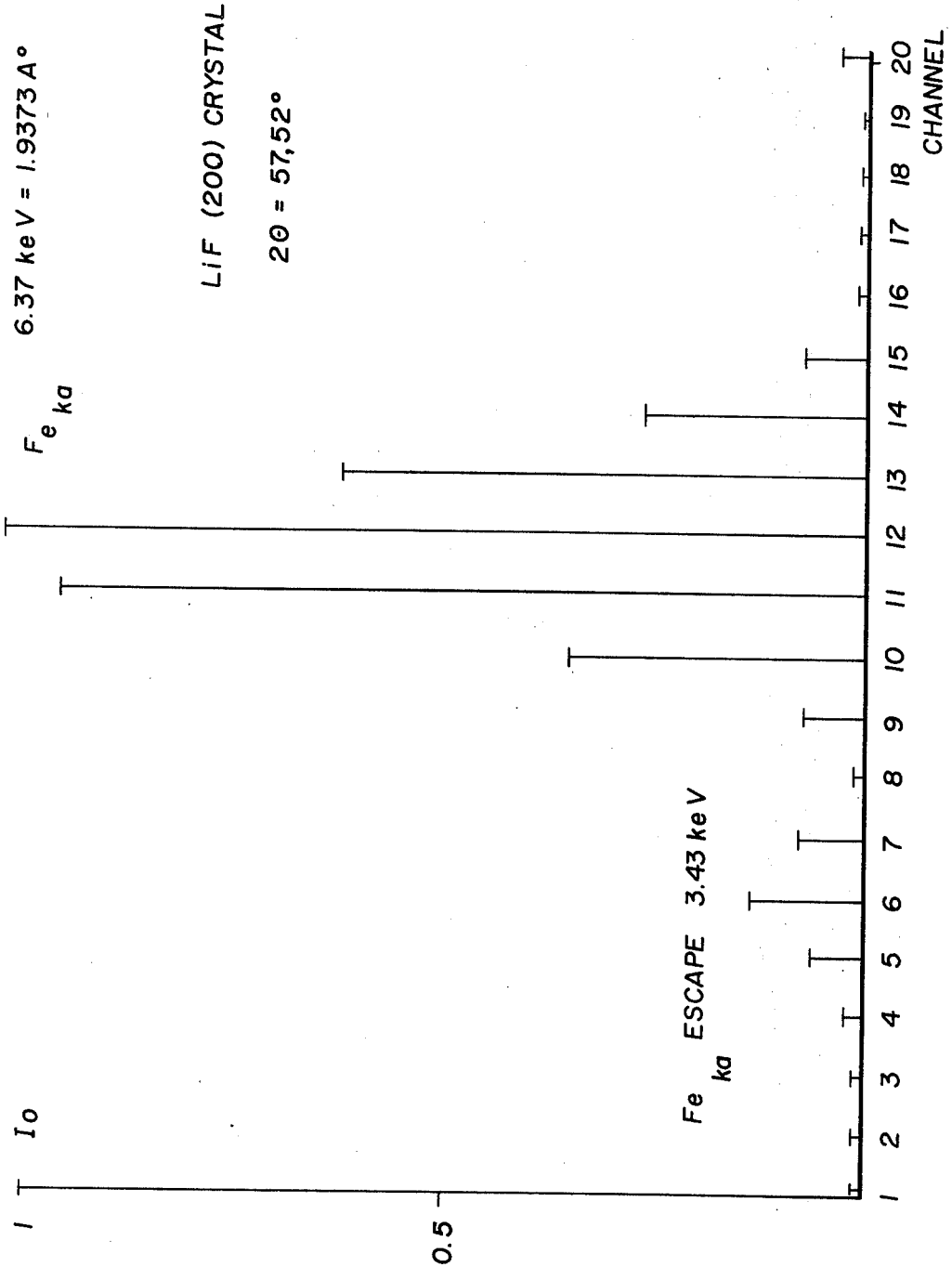
FIG. 3 is a graphical representation of measurements results such as are obtainable with a discriminator of the kind shown in FIG. 2 used in an apparatus according to FIG. 1.

FIG. 3 is a diagram of results that were obtained with a 20-channel discriminator in accordance with the present invention. In this case the X-ray fluorescence radiation of iron was measured with a lithium fluoride crystal (200 plane) at a refraction angle $2\theta = 57.52°$.

Figure 4:
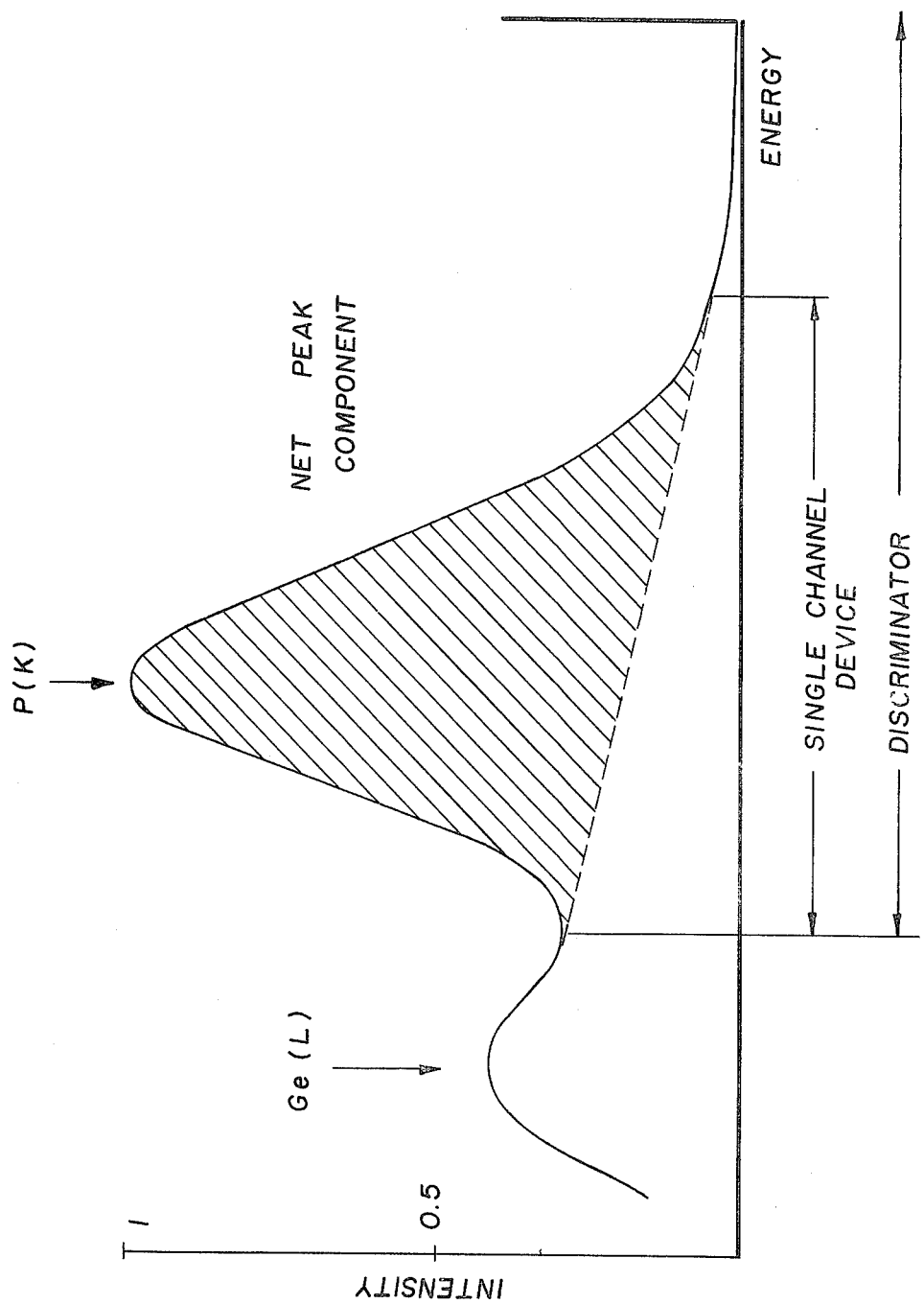
FIG. 4 is another graphical representation for explaining how results of the kind of FIG. 3 are evaluated.

FIG. 4 shows the possibility of easily evaluating result diagrams such as obtained in the case illustrated in FIG. 3. It is evident that the background radiation corresponding to the region below the broken straight line can easily be subtracted graphically or by means of the computer and that the shaded remainder surface below the pulse count envelope corresponds to the desired signal. The diagram of FIG. 4 illustrates the detection of a phosphor spectral line P(k) which was measured with a Germanium crystal (111 plane) and a pass-through counter tube. In the previously known equipment using a single-channel discriminator, the entire signal in the range designated "single channel" in FIG. 4 is lumped together and indicated as a single value. By the use of a multi-channel discriminator in accordance with the present invention, however, it is possible to obtain an exact energy profile and to subtract the disturbance component from the signal of interest.

Although the invention has been described with reference to a particular illustrative embodiment, variations are of course possible within the inventive concept. The multichannel peak voltage discriminator scheme, and the circuit of FIG. 2 may also be used in microbeam probe apparatus and method employing wavelength dispersive X-ray detection and in a fixed-channel X-ray fluorescence/spectrometer.

We claim:

1. Apparatus for analysis of X-ray fluorescence, comprising, in combination:
   means for causing a sample material to emit a beam of X-ray fluorescence;

a refraction crystal interposed in said beam for providing spectrometric angular dispersion of X-rays in a refracted beam in accordance with their wave length;

an angle-sensitive X-ray detector for detecting X-ray intensity with respect to wave length as represented by refraction angle in said beam and producing electric pulses at its output;

a multichannel peak voltage discriminator circuit having a plurality of channels each corresponding to a different range of pulse heights and having its input connected to the output of said detector for providing an output responsive to an input pulse only in that one of its multiplicity of output channels which corresponds to the voltage range in which the peak voltage of the input pulse lies, and means connected to each output channel of said multichannel peak voltage discriminator for producing a signal representative of the number of pulses produced in said output channel.

2. Apparatus as defined in claim 1 in which said multichannel peak voltage discriminator circuit (14) comprises a differential amplifier (22a to 22n) for each channel, the noninverting inputs of each of said differential amplifiers being connected to the input (20) of said discriminator circuit and the inverting inputs of said differential amplifiers being respectively connected to sources of respectively different bias voltages, and in which, further, the respective outputs of said differential amplifiers are connected to the respective setting inputs (S) of a corresponding multiplicity of bistable circuits (26a to 26n), in which, further, the positive and negative outputs of said bistable circuits are interconnected by a corresponding multiplicity of coincidence circuits (32a to 32n) each having a first input connected to the positive output of that bistable circuit having its second input connected to a corresponding differential amplifier, a second input, except in the case of the channel for the highest peak voltage, connected to the negative output of that bistable circuit having its input connected to the differential amplifier having its inverting input connected to the next higher bias voltage than that which is provided to the aforesaid corresponding differential amplifier and in which, further, a timing circuit (42, 43) is provided for providing timing pulses in response to pulses produced by said detector (12), said timing circuit having an input connected to the output of said detector (12), a first output (34) for providing an output timing pulse for said discriminator circuit (14) to an additional input of each of said coincidence circuits (32a to 32n) and a second output for producing a reset pulse after said output timing pulse has taken effect, said second output being connected to the reset inputs (RS) of each of said bistable circuits (26a to 26n).

3. An apparatus as defined in claim 2 in which each of said means connected to each output channel of said discriminator circuit (14) for producing a signal representative of a number of pulses produced in said output channel is a counter circuit (36a to 36n).

4. An apparatus as defined in claim 3 in which said timing circuit includes a pulse shaping and delay circuit (43) having its input connected to the input (20) of said discriminator circuit (14).

5. An apparatus as defined in claim 4 in which said timing circuit also includes a delay circuit (42) having its input connected to the output of said pulse shaping and delay circuit (43) and its output connected to the reset inputs (RS) of said bistable circuits (26a to 26n).

6. A method of analyzing X-ray fluorescence, comprising the steps of:

refracting a beam of X-ray fluorescence to be analyzed, by means of a pivoted crystal, towards an angle-sensitive X-ray intensity detector;

producing electric pulses in response to said X-ray beam, which pulses have a peak voltage representative of the X-ray energy and a rate of occurrence representative of X-ray intensity;

sorting said pulses with respect to their peak voltage in a multi-channel peak voltage discriminator so that the pulses appear in respective output channels corresponding to different pulse peak voltage ranges, and counting the number of pulses produced in each of said output channels during the same counting period.

7. A method as defined in claim 6 which comprises also the further step of recording or displaying on a common record or in a common display the number of pulses per unit of time produced in each of said output channels.

8. A microbeam probeam apparatus comprising a particle beam source and an X-ray analyzer section, wherein said analyzer section comprises a multichannel peak voltage discriminator circuit.

9. A microbeam probe apparatus as defined in claim 8, in which said multichannel peak voltage discriminator (14) comprises a differential amplifier (22a to 22n) for each channel, the noninverting inputs of each of said differential amplifiers being connected to the input (20) of said discriminator and the inverting inputs of said differential amplifiers being respectively connected to sources of respectively different bias voltages, and in which, further, the respective outputs of said differential amplifiers are connected to the respective settling inputs (S) if a corresponding multiplicity of bistable circuits (26a to 26n), in which, further, the positive and negative outputs of said bistable circuits are interconnected by a corresponding multiplicity of coincidence circuits (32a to 32n) each having a first input connected to the positive output of that bistable circuit having its second input connected to a corresponding differential amplifier, a second input, except in the case of the channel for the highest peak voltage, connected to the negative output of that bistable circuit having its input connected to the differential amplifier having its inverting input connected to the next higher bias voltage than that which is provided to the aforesaid corresponding differential amplifier and in which, further, a timing circuit (42, 43) is provided for providing timing pulses in response to pulses produced by said detector (12), said timing circuit having an input connected to the output of said detector (12), a first output (34) for providing an output timing pulse for said discriminator circuit (14) to an additional input of each of said coincidence circuits (32a to 23n) and a second output for producing a reset pulse after said output timing pulse has taken effect, said second output being connected to the reset inputs (RS) of each of said bistable circuits (26a to 26n).

10. A fixed channel X-ray fluorescence source spectrometer characterized by a detector portion wherein is provided a multichannel peak voltage detector circuit (14) which comprises a differential amplifier (22a to 22n) for each channel, noninverting inputs of each of said differential amplifiers being connected to the input (20) of said discriminator circuit and the inverting inputs of said differential amplifiers being respectively connected to sources of respectively different bias voltages, and in which, further, the respective outputs of said differential amplifiers are connected to the respective setting inputs (S) of a corresponding multiplicity of bistable circuits (26a to 26n), in which, further, the positive and negative outputs of said bistable circuits are interconnected by a corresponding multiplicity of coincidence circuits (32a to 32n) each having a first input connected to the positive output of that bistable circuit having its second input connected to a corresponding differential amplifier, a second input, except in the case of a channel for the highest peak voltage, connected to the negative output of that bistable circuit having its input connected to the differential amplifier having its inverting input connected to the next higher bias voltage than that which is provided to the aforesaid corresponding differential amplifier and in which, further, a timing circuit (42, 43) is provided for providing timing pulses in response to pulses produced by said detector (12), said timing circuit having an input connected to the output of said detector (12), a first output (34) for providing an output timing plus for said discriminator circuit (14) to an additional input of each of said coincidence circuits (32a to 32n) and a second output for producing a reset pulse after said output timing pulse has taken effect, said second output being connected to the reset inputs (RS) of each of said bistable circuits (26a to 26n).

* * * * *